US009107813B2

(12) United States Patent
O'Hagan et al.

(10) Patent No.: US 9,107,813 B2
(45) Date of Patent: Aug. 18, 2015

(54) IMMUNOGENIC COMPOSITIONS CONTAINING ANTHRAX ANTIGEN, BIODEGRADABLE POLYMER MICROPARTICLES, AND POLYNUCLEOTIDE-CONTAINING IMMUNOLOGICAL ADJUVANT (76) Inventors: Derek T. O'Hagan, Berkeley, CA (US); Manmohan Singh, Hercules, CA (US); Dennis M. Klinman, Potomac, MD (US)

(*) Notice: Subject to any disclaimer, the term of this patent is extended or adjusted under 35 U.S.C. 154(b) by 1604 days.

(21) Appl. No.: 11/667,642

(22) PCT Filed: Nov. 15, 2005

(86) PCT No.: PCT/US2005/041107
§ 371 (c)(1),
(2), (4) Date: Jan. 9, 2008

(87) PCT Pub. No.: WO2007/013893
PCT Pub. Date: Feb. 1, 2007

(65) Prior Publication Data
US 2008/0317784 A1 Dec. 25, 2008

Related U.S. Application Data (60) Provisional application No. 60/628,049, filed on Nov. 15, 2004.

(51) Int. Cl.
*A61K 39/07* (2006.01)
*A61K 39/02* (2006.01)
*A61K 45/00* (2006.01)
*A61K 9/00* (2006.01)
*A61K 39/00* (2006.01)
*A61K 9/16* (2006.01)

(52) U.S. Cl.
CPC .............. *A61K 9/0019* (2013.01); *A61K 9/167* (2013.01); *A61K 39/07* (2013.01); *A61K 9/1647* (2013.01); *A61K 39/00* (2013.01); *A61K 2039/55555* (2013.01); *A61K 2039/55561* (2013.01)

(58) Field of Classification Search
CPC ................................ A61K 39/00; A61K 39/07
USPC ....................... 424/184.1, 234.1, 246.1, 278.1
See application file for complete search history.

(56) References Cited

U.S. PATENT DOCUMENTS

| 6,086,901 | A | 7/2000 | O'Hagan et al. |
| 6,753,015 | B2 | 6/2004 | Fang et al. |
| 6,884,435 | B1 | 4/2005 | O'Hagan et al. |
| 2002/0025329 | A1 | 2/2002 | O'Hagan et al. |
| 2002/0136776 | A1 | 9/2002 | Fang et al. |
| 2003/0138453 | A1 | 7/2003 | O'Hagan et al. |
| 2004/0022814 | A1 | 2/2004 | O'Hagan et al. |
| 2004/0082530 | A1 | 4/2004 | Schmaljohn et al. |
| 2004/0101537 | A1 | 5/2004 | O'Hagan et al. |
| 2004/0156913 | A1 | 8/2004 | Fang et al. |
| 2005/0106178 | A1 | 5/2005 | O'Hagan |
| 2005/0118275 | A1 | 6/2005 | O'Hagan |
| 2005/0191319 | A1 | 9/2005 | O'Hagan et al. |
| 2005/0191358 | A1 | 9/2005 | O'Hagan et al. |
| 2005/0208143 | A1 | 9/2005 | O'Hagan et al. |
| 2005/0220883 | A1 | 10/2005 | O'Hagan et al. |

FOREIGN PATENT DOCUMENTS

| WO | WO 96/20698 | 7/1996 | |
| WO | WO 98/33487 | 8/1998 | ............... A61K 9/16 |
| WO | WO 00/06123 | 2/2000 | ............... A61K 9/16 |
| WO | WO 03/028661 A2 | 4/2003 | |
| WO | WO 2004/065578 A2 | 8/2004 | ......... A61K 31/7088 |
| WO | WO 2004/098491 A2 | 11/2004 | |
| WO | WO 2005/020964 A1 | 3/2005 | ............... A61K 9/50 |

OTHER PUBLICATIONS

Xie H. et al., "CpG oligodeoxynucleotides adsorbed onto polylactide-co-glycolide microparticles improve the immunogenicity and protective activity of the licensed anthrax vaccine," *Infect Immun*. Feb. 2005;73(2), pp. 828-833.
Hanna P., "Anthrax pathogenesis and host response," *Curr. Top. Microbiol. Immunol.*, 225, 1998, pp. 13-35.
Quinn C. P. et al., 98 A.D. Anthrax. *Topley and Wilson's Microbiology and Microbial Infections.*, M. Ballow and M. Sussman, eds. Collier, London, pp. 799-818., Date unknown, but before the date of instant application.
Lane H. C. et al., "Bioterrorism: a clear and present danger," *Nat. Med.*, 2001, vol. 7, No. 12, pp. 1271-1273.
Fish D.C. et al., "Purification and Properties of In Vitro-produced Anthrax Toxin Components", *J. Bacteriol*, vol. 95 No. 3, pp. 907-918.
Leppla S.H. et al., "Anthrax toxin edema factor: A bacterial edenylate dyclase that increases cyclic AMP concentrations in eukoryotic cells", *Proc. Natl. Acad. Sci., USA*, vol. 79, May 1982, pp. 3162-3166.
Mikesell P. et al., "Evidence for Plasmid-mediated Toxin Production in *Bacillus anthracis*" *Infect. Immun*. vol. 39, No. 1, Jan. 1983, pp. 371-376.
Welkos S.L. et al., "Sequence and analyses of the DNA encoding protective antigen of *Bacillus anthracis*", *Gene*, vol. 69, 1988, pp. 287-300.
Escuyer V. et al., "Structural homology between virulence-associated bacterial adenylate cyclases", *Gene*, vol. 71, 1988 pp. 293-298.
Bragg T.S. et al., "Nucleotide Sequence and analysis of the lethal factor gene (*lef*) from *Bacillus anthracis*", *Gene* vol. 81, 1989, pp. 45-54.

(Continued)

*Primary Examiner* — Rodney P Swartz
(74) *Attorney, Agent, or Firm* — Helen Lee (57) ABSTRACT

Immunogenic compositions and kits, as well as methods of stimulating immune responses and methods of immunization using the same. The compositions and kits comprise: (a) an antigen derived from *Bacillus anthracis*; (b) polymer microparticles comprising a biodegradable polymer; and (c) a polynucleotide-containing immunological adjuvant.

25 Claims, 4 Drawing Sheets

(56) References Cited

OTHER PUBLICATIONS

Coeshott C.M. et al., "Pluronic F127-based systemic vaccine delivery systems," Vaccine, 2004 Jun. 23, vol. 22, (19), pp. 2396-2405.
Ivins B.E. et al., "Recent advances in the development of an improved, human anthrax vaccine," Eur.J Epidemiol, vol. 4, No. 1, Mar. 1988, pp. 12-19.
Ivins B.E. et al., "Immunization against anthrax with Bacilus anthracis protective antigen combined with adjuvants," Infect Immun,, vol. 60, No. 2, Feb. 1992, pp. 662-668.
Welkos S.L. et al., "Comparative safety and efficacy against Bacillus anthracis of protective antigen and live vaccines in mice," Microb. Pathog., vol. 5, 1988, pp. 127-139.
Little S.F. et al., "Molecular pathogenesis of Bacillus anthracis infection," Microbes.Infect., 2, 1999, pp. 131-139.
Welkos S. et al., "The role of antibodies to Bacillus anthracis and anthrax toxin components in inhibiting the early stages of infection by anthrax spores," Microbiology, vol. 147, 2001, pp. 1677-1685.
Pittman P. R. et al., "Anthrax vaccine: short-term safety experience in humans," Vaccine, vol. 20, 2002, pp. 972-978.
Pittman P.R. et al., "Anthrax vaccine: immunogenicity and safety of a dose-reduction, route-change comparison study in humans," Vaccine, vol. 20, 2002, pp. 1412-1420.
Geier D.A. et al., "Anthrax vaccination and joint related adverse reactions in light of biological warfare scenarios," Clin.Exp. Rheumatol., vol. 20, 2002, pp. 217-220.
Ready T., "US soldiers refuse to fall in line with anthrax vaccination scheme," Nat.Med., 10, Feb. 2004, p. 112.
Davis H.L. et al., "CpG DNA overcomes hyporesponsiveness to hepatitis B vaccine in orangutans," Vaccine, vol. 18, 2000, pp. 1920-1924.
Jones T.R. et al., "Synthetic oligodeoxynucleotides containing CpG motifs enhance immunogenicity of a peptide malaria vaccine in Aotus monkeys," Vaccine, vol. 17, 1999, pp. 3065-3071.
Verthelyi D. et al., "CpG oligodeoxynucleotides as vaccine adjuvants in primates," J.Immunol., 168, 2002, pp. 1659-1663.
Klinman D.M., et al., "CpG Oligonucleotides Improve the Protective Immune Response Induced by the Anthrax Vaccination of Rhesus Macaques," Vaccine, vol. 22, 2004, pp. 2881-2886.
Klinman D.M., "Immunotherapeutic uses of CpG oligodeoxynucleotides," Nat.Rev.Immunol., vol. 4, Apr. 2004, pp. 1-10.
Krieg A.M. et al., "CpG motifs in bacterial DNA trigger direct B-cell activation," NAT, 374, Apr. 6, 1995, pp. 546-549.
Klinman D.M.et al., "CpG motifs present in bacterial DNA rapidly induce lymphocytes to secrete interleukin 6, interleukin 12 and interferon γ", Proc.Natl.Acad.Sci. USA, 93, Apr. 1996, pp. 2879-2883.
Ballas Z.K. et al., "Induction of NK activity in murine and human cells by CpG motifs in oligodeoxynucleotides and bacterial DNA," J.Immunol., vol. 157, 1996, pp. 1840-1845.
Halpern M.D. et al., "Bacterial DNA induces murine interferon-γ production by stimulation of interleukin-12 and tumor necrosis factor-α," Cell.Immunol., vol. 167, 1996, pp. 72-78.
Singh M. et al., "Cationic microparticles are an effective delivery system for immune stimulatory cpG DNA," Pharm.Res., 18, Oct. 2001, No. 1, pp. 1476-1479.
Singh M. et al., "Charged polylactide co-glycolide microparticles as antigen delivery systems," Expert.Opin.Biol Ther., 4, 2004, pp. 483-491.
Singh M. et al., "Controlled release microparticles as a single dose hepatitis B vaccine: evaluation of immunogenicity in mice," Vaccine, 15, No. 5, 1997, pp. 475-481.
Briones M.et al., "The preparation, characterization, and evaluation of cationic microparticles for DNA vaccine delivery," Pharm.Res., vol. 18, No. 5, 2001, pp. 709-712.
Denis-Mize K. S. et al., "Mechanisms of increased immunogenicity for DNA-based vaccines adsorbed onto cationic microparticles," Cell Immunol., 225, 2003, pp. 12-20.
Denis-Mize K. S. et al., "Plasmid DNA adsorbed onto cationic microparticles mediates target gene expression and antigen presentation by dendritic cells," Gene Ther., 7, 2000, pp. 2105-2112.
O'Hagan D. et al., "Induction of potent immune responses by cationic microparticles with adsorbed human immunodeficiency virus DNA vaccines," J. Virol., vol. 75, No. 19, 2001, pp. 9037-9043.
Gursel I. et al., "Sterically stabilized cationic liposomes improve the uptake and immunostimulatory activity of CpG oligonucleotides," J. Immunol., 167, 2001, pp. 3324-3328.
Ivins B. E. et al., "Comparative efficacy of experimental anthrax vaccine candidates against inhalation anthrax in rhesus macaques," Vaccine, 16, No. 11/12, 1998, pp. 1141-1148.
Ivins B. E. et al., "Immunization against anthrax with aromatic compound-dependent (Aro⁻) mutants of Bacillus anthracis and with recombinant strains of Bacillus subtilis that produce anthrax protective antigen," Infect.Immun., vol. 58, No. 2, Feb. 1990, pp. 303-308.
Oishi K. et al., "Antibacterial and protective properties of monoclonal antibodies reactive with Escherichia coli O111:B4 lipopolysaccharide: relation to antibody isotype and complement-fixing activity," J Infect .Dis., 165, 1992, pp. 34-45.
Klinman D. M. et al., "CpG motifs as immune adjuvants," Vaccine, 17, 1999, pp. 19-25.
Davis H. L. et al., "CpG DNA is a potent enhancer of specific immunity in mice immunized with recombinant hepatitis B surface antigen," J. Immunol., 160, 1998, pp. 870-876.
Halperin S. A. et al., "A phase I study of the safety and immunogenicity of recombinant hepatitis B surface antigen co-administered with an immunostimulatory phosphorothioate oligonucleotide adjuvant," Vaccine, 21, 2003, pp. 2461-2467.
Vajdy M. et al., "Microparticles for intranasal immunization," Adv. Drug Deliv. Rev., 51, 2001, pp. 127-141.
Valiante N. M. et al., "Innate immunity and biodefence vaccines," Cell Microbiol., 5(11), 2003, pp. 755-760.
Sanceau J. et al., "Triggering of the human interleukin-6 gene by interferon-γ and tumor necrosis factor-α in monocytic cells involves cooperation between interferon regulatory factor-1, NF-κB, and Sp1 transcription factors," J Biol Chem., vol. 270, No. 46, Nov. 17, 1995, pp. 27920-27931.
Little S. F. et al., "Defining a serological correlate of protection in rabbits for a recombinant anthrax vaccine," Vaccine, 22, 2004, pp. 422-430.
Flick-Smith H.C. et al., "Mucosal or Parenteral Administration of Microsphere-Associated Bacillus anthracis Protective Antigen Protects against Anthrax Infection in Mice," Infection and Immumity, American Society for Microbiology Washington, US, vol. 70, No. 4, Apr. 2002, pp. 2022-2028.
Edelman. "The Development and Use of Vaccine Adjuvants," Molecular Biotechnology, 21:129-148 (2002).
Malyala et al., "The Potency of the Adjuvant, CpG Oligos, Is Enhanced by Encapsulation in PLG Microparticles," Journal of Pharmaceutical Sciences, 97:1155-1164 (2008).
Spickler et al., "Adjuvants in Veterinary Vaccines Modes of Action and Adverse Effects," J Vet Intern Med, 17:273-281 (2003).

IMMUNOGENIC COMPOSITIONS CONTAINING ANTHRAX ANTIGEN, BIODEGRADABLE POLYMER MICROPARTICLES, AND POLYNUCLEOTIDE-CONTAINING IMMUNOLOGICAL ADJUVANT

STATEMENT OF RELATED APPLICATION

This application claims the benefit of U.S. Provisional Patent Application 60/628,049, filed Nov. 15, 2004, entitled "Immunogenic Compositions Containing Anthrax Antigen, Biodegradable Polymer Microparticles, and Polynucleotide-Containing Immunological Adjuvant", which is incorporated herein by reference in its entirety.

FIELD OF THE INVENTION

The present invention relates to immunogenic pharmaceutical compositions, particularly vaccine compositions.

BACKGROUND

Bacillus anthracis is an aerobic gram-positive spore-forming bacterium found naturally in wild and domesticated animals. Hanna, P. 1998. Curr. Top. Microbiol. Immunol. 225: 13-35. It is highly resistant to environmental degradation, and it produces a tripartite toxin that reduces the ability of the host=s immune system to eliminate the pathogen. Id. Human exposure to anthrax typically arises following contact with infected livestock, and generally results in a mild form of cutaneous disease. Friedlander, A. M., and P. S. Brachman. 1998. Anthrax, p. 729-739. In S. A. Plotkin and E. A. Mortimer (ed.), Vaccines. W. B. Saunders, Philadelphia, Pa. Quinn, C. P. and P. C. Turnbull. 98 A.D. Anthrax, p. 799-818. In M. Ballow and M. Sussman (ed.), Topley and Wilson's Microbiology and Microbial Infections, Collier, London. However, anthrax spores designed for aerosol delivery were intentionally released by bioterrorists in the US in 2001. The resultant morbidity, mortality, and widespread panic underscored the potential for anthrax to be used as a bioterror agent as well as the need to improve the speed, magnitude and safety of anthrax vaccination. Lane, H. C., et al. Nat. Med. 7:1271-1273.

As noted in U.S. Patent Application 2004/0082530, the pathogenicity of B. anthracis is expressed in two ways: a toxic effect made evident by the appearance of an edema, and a so-called lethal toxic effect which may lead to death in infected individuals. There are two main virulence factors possessed by B. anthracis, a poly-D-glutamic capsule that inhibits phagocytosis and two binary toxins which are formed from combinations selected from three protein factors. These two binary toxins possess a common cell receptor-binding component which, when combined with either one of the other two factors forms an active toxin. The binding component present in both of the active toxins is non-toxic and is involved in the binding of the B. anthracis toxins to cell membranes in an infected host. The other two protein factors constitute the active elements responsible for the manifestation of either the toxic effect of the edema type or the toxic effect with lethal character. These two active factors are termed edematogenic factor (EF) and lethal factor (LF). The non-toxic factor responsible for binding to cell membranes is called protective antigen (PA) since, during immunization assays, the capacity to confer active protection against the disease was initially attributed to this factor. The three factors PA, LF and EF have been isolated and purified as reported by Fish et al. (1968) J. Bacteriol. 95:907-917, and the two toxins obtained by the combination of PA and LF and of PA and EF, have been characterized and described by Leppla et al. (1982) Proc. Natl. Acad. Sci. USA 79:3162-3166. The B. anthracis genes pag, cya and lef that encode the factors PA, EF and LF, respectively, are distributed on a plasmid termed "pX01" of B. anthracis, as described by Mikesell et al (1983) Infect. Immun. 39:371-376. In addition, the pag, cya and lef genes have been cloned and fully sequenced as described by Welkos et al. (1988) Gene 69:287-300; Escuyer et al. (1988) Gene 71:293-298; and Bragg et al. (1989) Gene 81:45-54.

Anthrax Vaccine Adsorbed (AVA) is the only anthrax vaccine licensed for human use in the U.S. It is prepared by adsorbing the culture filtrate of an attenuated toxinogenic non-encapsulated strain of B. anthracis (V770-NP1-R) onto aluminum hydroxide. Ivins, B. E., and S. L. Welkos. 1988. Eur. J. Epidemiol. 4:12-19. Studies show that protective antigen (PA), the core of anthrax toxin, is the major immunogen of AVA. Antibodies (Ab) against PA neutralize the toxin, inhibit spore germination, and improve the phagocytosis/killing of spores by macrophages. Ivins, B. E., et al. 1992. Infect. Immun. 60:662-668. Little, S. F., and B. E. Ivins. 1999. Microbes. Infect. 1:131-139. Welkos, S., et al. 2001. Microbiology 147:1677-1685. Welkos, S. L., and A. M. Friedlander. 1988. Microb. Pathog. 5:127-139. Vaccination with AVA requires a series of 6 immunizations delivered over 18 months followed by yearly boosters. Pittman, P. R., et al. 2001. Vaccine 20:972-978. Pittman, P. R., et al. 2002. Vaccine 20:1412-1420. This schedule has been linked to the development of adverse side effects including joint pain, gastrointestinal disorders, and pneumonia, leading many U.S. soldiers to refuse vaccination. Geier, D. A., and M. R. Geier. 2002. Clin. Exp. Rheumatol. 20:217-220. Ready, T. 2004. Nat. Med. 10:112. Strategies which reduce the dose and number of AVA immunizations required to achieve protection are expected to improve compliance.

SUMMARY OF THE INVENTION

According to an aspect of the invention, immunogenic kits and compositions are provided which comprise: (a) a first composition comprising an antigen derived from Bacillus anthracis; (b) a second composition comprising biodegradable polymer microparticles and (c) a third composition comprising a polynucleotide-containing immunological adjuvant, wherein the first, second, and third compositions may be the same or different compositions.

For example, in one embodiment of the present invention, an immunogenic composition is provided, which comprises: an antigen derived from Bacillus anthracis, biodegradable polymer microparticles and a polynucleotide-containing immunological adjuvant. In another embodiment, an immunogenic kit is provided which comprises: one composition comprising an antigen derived from Bacillus anthracis; another separate composition comprising biodegradable polymer microparticles; and yet another separate composition comprising a polynucleotide-containing immunological adjuvant. In still another embodiment, an immunogenic kit is provided which comprises: one composition comprising an antigen derived from Bacillus anthracis; and another separate composition comprising biodegradable polymer microparticles and a polynucleotide-containing immunological adjuvant.

The polymer microparticles for use in conjunction with the present invention comprise a biodegradable polymer, for example, a polymer selected from a poly(α-hydroxy acid), a polyhydroxy butyric acid, a polycaprolactone, a polyorthoester, a polyanhydride, a polycyanoacrylate, or a mixture of the same, among others. The microparticles may be prepared via a variety of techniques, several of which are described below. In various embodiments, the microparticles are formed from a poly(α-hydroxy acid), such as a poly(lactide) ("PLA"), a copolymer of lactide and glycolide, e.g., poly(D,L-lactide-co-glycolide) ("PLG"), or a copolymer of D,L-lactide and caprolactone. Poly(D,L-lactide-co-glycolide) polymers include those having a lactide:glycolide molar ratio ranging, for example, from 20:80 to 80:20, from 25:75 to 75:25, from 40:60 to 60:40, or from 55:45 to 45:55, among others, and having a molecular weight ranging, for example, from 5,000 to 200,00 Daltons, from 10,000 to 100,000 Daltons, from 20,000 to 70,000 Daltons, or from 40,000 to 50,000 Daltons, among others.

Antigens for use in conjunction with the represent invention can be derived from a variety of *Bacillus anthracis* strains, including strain V770-NP1-R, and include killed, attenuated or inactivated organisms as well as subunit antigens. The antigens include polypeptide containing species, such as proteins and oligopeptides, polysaccharide containing species, and polynucleotide containing species which express an immunogenic protein or polypeptide.

Polynucleotide-containing immunological adjuvants for use in conjunction with the compositions and kits of the present invention include DNA- and RNA-containing immunological adjuvants, such as oligodeoxynucleotides and double-stranded RNA, among others.

The compositions and kits of the present invention also optionally include supplemental immunological adjuvants beyond polymer microparticles and polynucleotide-containing immunological adjuvants, examples of which include, among others, (a) aluminum salts (alum), such as aluminum hydroxide, aluminum phosphate, aluminum sulfate, etc., (b) *E. coli* heat-labile toxins, (c) liposaccharide phosphate compounds (e.g., monophosphorylipid A and its derivatives) and liposaccharide phosphate mimetics, and (d) submicron emulsions comprising a metabolizable oil, such as squalene, and an emulsifying agent, such as one or more sorbitan derivatives (e.g., MF59).

Further embodiments of the invention are directed to methods of delivering *Bacillus anthracis* antigens to a host animal, which comprises administering to the host animal any of the immunogenic compositions and kit components described herein. The host animal is preferably a vertebrate animal, more preferably a mammal, and even more preferably a human.

The present invention is also directed to methods of stimulating an immune response in a host animal, comprising administering to the animal any of the immunogenic compositions and kit components described herein in an amount effective to induce the immune response.

The present invention is further directed to methods of immunizing a host animal against *Bacillus anthracis* comprising administering to the animal any of the immunogenic compositions and kit components described herein in an amount effective to induce a protective response.

Delivery of the immunogenic compositions and kit components of the invention may be performed by any known pharmaceutically effective method, including direct injection (e.g., subcutaneously, intraperitoneally, intravenously or intramuscularly), mucosal delivery, among others.

Many of the above and further aspects of the present invention are enumerated in the following paragraphs:

Aspect 1. An immunogenic composition comprising: (a) an antigen derived from *Bacillus anthracis*; (b) polymer microparticles comprising a biodegradable polymer; and (c) a polynucleotide-containing immunological adjuvant.

Aspect 2. The immunogenic composition of Aspect 1, wherein the antigen is derived from *Bacillus anthracis* strain V770-NP1-R.

Aspect 3. The immunogenic composition of Aspect 1, wherein the antigen comprises killed or attenuated *Bacillus anthracis*.

Aspect 4. The immunogenic composition of Aspect 1, wherein the antigen comprises an attenuated toxinogenic non-encapsulated *Bacillus anthracis*.

Aspect 5. The immunogenic composition of Aspect 1, wherein the antigen comprises a subunit antigen.

Aspect 6. The immunogenic composition of Aspect 5, wherein the subunit antigen is a polypeptide containing antigen.

Aspect 7. The immunogenic composition of Aspect 1, wherein the antigen comprises a vector construct that encodes a polypeptide-containing antigen.

Aspect 8. The immunogenic composition of any of Aspects 1-7, wherein the antigen is adsorbed onto microparticles.

Aspect 9. The immunogenic composition of Aspect 8, wherein the antigen is adsorbed onto aluminum hydroxide microparticles.

Aspect 10. The immunogenic composition of Aspect 1, wherein the antigen comprises attenuated toxinogenic non-encapsulated *Bacillus anthracis*, at least a portion of which is adsorbed onto aluminum hydroxide.

Aspect 11. The immunogenic composition of any of Aspects 1-10, wherein the immunogenic composition further comprises a surfactant.

Aspect 12. The immunogenic composition of Aspect 11, wherein the surfactant comprises a cationic surfactant.

Aspect 13. The immunogenic composition of Aspect 11, wherein the surfactant comprises an anionic surfactant.

Aspect 14. The immunogenic composition of any of Aspects 1-13, wherein the microparticles have an average diameter between 500 nanometers and 20 microns.

Aspect 15. The immunogenic composition of any of Aspects 1-14, wherein the biodegradable polymer is selected from a poly(α-hydroxy acid), a polyhydroxy butyric acid, a polycaprolactone, a polyorthoester, a polyanhydride, and a polycyanoacrylate.

Aspect 16. The immunogenic composition of Aspect 15, wherein the biodegradable polymer is a poly(α-hydroxy acid).

Aspect 17. The immunogenic composition of Aspect 16, wherein the biodegradable polymer is a poly(lactide-co-glycolide).

Aspect 18. The immunogenic composition of Aspect 17, wherein the biodegradable polymer is a poly(lactide-co-glycolide) having a lactide:glycolide molar ratio ranging from 40:60 to 60:40.

Aspect 19. The immunogenic composition of any of Aspects 1-18, wherein at least a portion of the polynucleotide-containing immunological adjuvant is entrapped within the microparticles.

Aspect 20. The immunogenic composition of any of Aspects 1-18, wherein at least a portion of the polynucleotide-containing immunological adjuvant is adsorbed onto the microparticles.

Aspect 21. The immunogenic composition of any of Aspects 1-20, wherein the polynucleotide-containing immunological adjuvant comprises an oligonucleotide immunological adjuvant.

Aspect 22. The immunogenic composition of any of Aspects 1-20, wherein the polynucleotide-containing immunological adjuvant comprises an oligodeoxynucleotide immunological adjuvant.

Aspect 23. The immunogenic composition of any of Aspects 1-120, wherein the polynucleotide-containing immunological adjuvant is a CpG oligonucleotide.

Aspect 24. The immunogenic composition of any of Aspects 1-20, wherein the polynucleotide-containing immunological adjuvant is a CpG oligodeoxynucleotide.

Aspect 25. The immunogenic composition of any of Aspects 1-8 and 11-24, further comprising a supplemental immunological adjuvant.

Aspect 26. The immunogenic composition of Aspect 25, wherein the supplemental immunological adjuvant is an aluminum salt.

Aspect 27. The immunogenic composition of Aspect 25, wherein the supplemental immunological adjuvant is selected from (a) $E.\ coli$ heat-labile toxins, (b) liposaccharide phosphate compounds, and (c) submicron emulsions comprising squalene and an emulsifying agent.

Aspect 28. The immunogenic composition of any of Aspects 1-27, wherein the immunogenic composition is an injectable composition.

Aspect 29. A method of immunizing a vertebrate host animal against infection by $Bacillus\ anthracis$ comprising administering to the animal the immunogenic composition of any of Aspects 1-28.

Aspect 30. A method of stimulating an immune response in a vertebrate host animal, comprising administering to the host animal the immunogenic composition of any of Aspects 1-28.

Aspect 31. The method of any of Aspects 29-30, wherein the vertebrate host animal is human.

Aspect 32. An immunogenic kit comprising: (a) a first composition comprising an antigen derived from $Bacillus\ anthracis$; (b) a second composition comprising biodegradable polymer microparticles and (c) a third composition comprising a polynucleotide-containing immunological adjuvant, wherein the first, second, and third compositions may be different from one another, wherein the first and second compositions may be the same and the third composition different, wherein the first and third compositions may be the same and the second composition different, or wherein the second and third compositions may be the same and the third composition different.

Aspect 33. The immunogenic kit of Aspect 32, wherein the second and third compositions are the same and the third composition is different.

Aspect 34. The immunogenic kit of Aspect 33, wherein at least a portion of the polynucleotide-containing immunological adjuvant is adsorbed to the polymer microparticles.

Aspect 35. The immunogenic kit of Aspect 33, further comprising aluminum hydroxide microparticles, wherein the antigen is adsorbed to the aluminum hydroxide microparticles, wherein the polynucleotide-containing immunological adjuvant comprises CpG oligonucleotide, and wherein at least a portion of the CpG oligonucleotide is adsorbed to the polymer microparticles.

Aspect 36. A method of immunizing a vertebrate host animal against infection by $Bacillus\ anthracis$ comprising administering to the animal the compositions of the kit of any one of Aspects 32-35.

Aspect 37. A method of stimulating an immune response in a vertebrate host animal, comprising administering to the animal the compositions of the kit of any one of Aspects 32-35.

Aspect 38. The method of any one of Aspects 36-37, wherein the vertebrate host animal is human.

One advantage of the present invention is immune responses to $Bacillus\ anthracis$ in vertebrate subjects can be boosted and accelerated.

Another advantage of the present invention is that protective immunity against $Bacillus\ anthracis$ can be generated quickly in vertebrate subjects.

The above and various other aspects, embodiments, and advantages of the present invention will become readily apparent to those of ordinary skill in the art in view of the disclosure herein and the appended claims.

DETAILED DESCRIPTION OF THE INVENTION

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Handbook of Surface and

*Colloidal Chemistry* (Birdi, K. S., ed, CRC Press, 1997) and *Seymour/Carraher=s Polymer Chemistry* (4th edition, Marcel Dekker Inc., 1996).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "microparticle" refers to one or more microparticles, and the like.

Unless the context indicates otherwise, all percentages and ratios herein are given on a weight basis.

A. Definitions

In describing the present invention, the following terms will be employed, and are intended to be defined as indicated below.

The term "microparticle" as used herein, refers to a particle of about 10 nm to about 150 μm in diameter, more typically about 200 nm to about 30 μm in diameter, and even more typically about 500 nm to about 10-20 μm in diameter. The microparticles of the present invention may aggregate into larger masses under some circumstances. The microparticle will generally be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Polymer microparticles for use herein are typically formed from materials that are sterilizable, substantially non-toxic, and biodegradable. Such materials include poly(α-hydroxy acids), polyhydroxybutyric acids, polycaprolactones, polyorthoesters, polyanhydrides, and polycyanoacrylates (e.g., polyalkylcyanoacrylate or "PACA"). More typically, microparticles for use with the present invention are polymer microparticles derived from poly(α-hydroxy acids), for example, from a poly(lactide) ("PLA") or a copolymer of lactide and glycolide, such as a poly(D,L-lactide-co-glycolide) ("PLG"), or a copolymer of D,L-lactide and caprolactone. The polymer microparticles may be derived from any of various polymeric starting materials which have a variety of molecular weights and, in the case of the copolymers such as PLG, a variety of monomer (e.g., lactide:glycolide) ratios, the selection of which will be largely a matter of choice, depending in part on the coadministered species. These parameters are discussed further below.

The term "surfactant" as used herein includes detergents, dispersing agents, suspending agents, and emulsion stabilizers. Cationic surfactants include, but are not limited to, cetyltrimethylammonium bromide or "CTAB" (e.g., cetrimide), benzalkonium chloride, DDA (dimethyl dioctodecyl ammonium bromide), DOTAP (dioleoyl-3-trimethylammonium-propane), chitosan and the like. Anionic surfactants include, but are not limited to, SDS (sodium dodecyl sulfate), SLS (sodium lauryl sulfate), DSS (disulfosuccinate), sulphated fatty alcohols, and the like. Nonionic surfactants include, but are not limited to, PVA, povidone (also known as polyvinylpyrrolidone or PVP), sorbitan esters, polysorbates, polyoxyethylated glycol monoethers, polyoxyethylated alkyl phenols, poloxamers, and the like.

The term "submicron emulsion" as used herein refers to an oil-in-water emulsion comprising oil droplets, substantially all of which range in size up to 1000 nm, for example, from 10 nm to 1000 nm.

The term "pharmaceutical" refers to biologically active compounds such as antibiotics, antiviral agents, growth factors, hormones, antigens and the like.

The term "adjuvant" refers to any substance that assists or modifies the action of a pharmaceutical. Adjuvants include, but are not limited to immunological adjuvants, which lead to one or more of the following effects, among others: an increased immune response, a more diversified immune response, an accelerated immune response, a more persistent/prolonged immune response, and so forth.

A "polynucleotide" is a synthetic or natural nucleic acid polymer. A polynucleotide can include as little as two nucleotides. An "oligonucleotide" is a polynucleotide of relatively low molecular weight, typically containing from 2 to 500 nucleotides. Polynucleotides include both double- and single-stranded sequences and refer to, but are not limited to, genomic DNA, mRNA, cDNA from mRNA, double-stranded RNA (dsRNA) and CpG oligonucleotides, among others. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As used herein, the phrase "nucleic acid" refers to DNA, RNA, or chimeras formed therefrom.

By saying that a species is a "polynucleotide-containing species" is meant that the species is a molecule, at least a portion of which is a polynucleotide.

As used herein, the phrases "oligonucleotide comprising at least one CpG motif" and "CpG oligonucleotide" refer to a polynucleotide comprising at least one CpG dinucleotide. Oligonucleotides comprising at least one CpG motif can comprise multiple CpG motifs. As used herein, the phrase "CpG motif" refers to a dinucleotide portion(s) of an oligonucleotide, which comprises a cytosine nucleotide followed by a guanosine nucleotide. Guanosine and cytosine analogs, such as 5-methylcytosine, can also be used in place of guanosine and cytosine. CpG oligonucleotides vary widely in size ranging, for example, between 2, 5, 10, 20, 50, 100, 200 and 500 nucleotides.

A "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form. An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide"

also refers to a monosaccharide polymer that contain two or more linked monosaccharides. To avoid any ambiguity, the second definition is to be applied at all times, unless there are explicit indications to the contrary. The monosaccharides are typically linked by glycosidic linkages. Both full-length, naturally occurring polysaccharides and fragments thereof are encompassed by the definition. The terms also include modifications, such as deletions, additions and substitutions to native polysaccharide sequences.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

The terms "polypeptide" and "protein" refer to polymers of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins such as glycoproteins, saccharide antigens conjugated to carrier proteins, and so forth.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens, it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

A polypetide epitope can include, for example, between about 5-15 amino acids. Epitopes of a given antigen can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

Where a saccharide or carbohydrate antigen is used, it may be conjugated to a carrier protein in order to enhance immunogenicity as is known in the vaccine art. Preferred carrier proteins are bacterial toxins or toxoids, such as diphtheria or tetanus toxoids. Other suitable carrier proteins include *N. meningitidis* outer membrane protein (European patent application 0372501), synthetic peptides (European patent application 0378881; European patent application 0427347), heat shock proteins (International patent application WO93/17712), pertussis proteins (International patent application WO98/58668; European patent application 0471177), protein D from *H. Influenzae* (International patent application WO00/56360), toxin A or B from *C. difficile* (International patent application WO00/61761), and so forth. Any suitable conjugation reaction can be used, with any suitable linker, where necessary. Toxic protein antigens may be detoxified where necessary (e.g. detoxification of pertussis toxin by chemical and/or means (Rappuoli et al. (1991) *TIBTECH* 9:232-238).

The term "antigen" as used herein denotes both subunit antigens, i.e., antigens which are separate and discrete from a whole organism with which the antigen is associated in nature, as well as killed, attenuated or inactivated organisms. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide that expresses an immunogenic protein, or antigenic determinant in vivo, such as in nucleic acid immunization applications, is also included in the definition of antigen herein.

Furthermore, for purposes of the present invention, an "antigen" refers to a protein, which includes modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition such as an immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

The immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered, or because the composition provokes a more persistent/prolonged immune response, because the composition more rapidly provokes an immune response, and so forth. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of infection by a pathogen or the prevention of a disorder, (ii) the reduction or elimination of symptoms associated with a pathogen or disorder, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer element(s), locus defining element(s), or other element(s) which control(s) gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. A preferred pCMV vector is one which contains the immediate-early enhancer/promoter of CMV and a bovine growth hormone terminator. It is described in detail in Chapman, B. S., et al. 1991. "Effect of intron A from human cytomegalovirus (Towne) immediate-early gene on heterologous expression in mammalian cells." Nucleic Acids Res. 19:3979-86.

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Patent Applications WO 97/38087, WO 99/18226 and commonly owned WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. General Methods

1. Microparticles

Useful polymers for forming microparticles for the immunogenic compositions described herein include homopolymers, copolymers and polymer blends derived from the following: polyhydroxybutyric acid (also known as polyhydroxybutyrate); polyhydroxy valeric acid (also known as polyhydroxyvalerate); polyglycolic acid (PGA) (also known as polyglycolide); polylactic acid (PLA) (also known as polylactide); polydioxanone; polycaprolactone; polyorthoester; and polyanhydride. More typical are poly($\alpha$-hydroxy acids), such as poly(L-lactide), poly(D,L-lactide) (both referred to as APLA" herein), poly(hydroxybutyrates), copolymers of lactide and glycolide, such as poly(D,L-lactide-co-glycolides) (designated as "PLG" herein), or copolymers of D,L-lactide and caprolactone.

The above polymers are available in a variety of molecular weights, and the appropriate molecular weight for a given use is readily determined by one of skill in the art. Thus, for example, a suitable molecular weight for PLA may be on the order of about 2000 to 5000. A suitable molecular weight for PLG may range from about 10,000 to about 200,000, typically about 15,000 to about 150,000.

Where copolymers are used, copolymers with a variety of monomer ratios may be available. For example, where PLG is used to form the microparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. Mixtures of microparticles with varying lactide:glycolide ratios may also find use herein in order to achieve desired release kinetics. Degradation rate of the microparticles of the present invention can also be controlled by such factors as polymer molecular weight and polymer crystallinity.

PLG copolymers with varying lactide:glycolide ratios and molecular weights are readily available commercially from a number of sources including from Boehringer Ingelheim, Germany and Birmingham Polymers, Inc., Birmingham, Ala. Some exemplary PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of 34,000 Da; (c) RG 504, a PLG having a 50:50 lactide/glycolide molar ratio and a molecular weight of 48,000 Da, (d) RG 752, a PLG having a 75:25 lactide/glycolide molar ratio and a molecular weight of 22,000 Da; and (e) RG 755, a PLG having a 75:25 lactide/glycolide molar ratio and a molecular weight of 68,000 Da. PLG polymers can also be synthesized by simple polycondensation of the lactic acid component using techniques well known in the art, such as described in Tabata et al., *J. Biomed. Mater. Res*. (1988) 22:837-858.

Where used, poly(D,L-lactide-co-glycolide) polymers are typically those having a molar lactide/glycolide molar ratio ranging from 20:80 to 80:20, more typically 40:60 to 60:40, and having a molecular weight ranging from 10,000 to 100,000 Daltons, more typically from 20,000 Daltons to 70,000 Daltons.

Biodegradable microparticles can be thought of as a particular type of immunological adjuvant. Biodegradable microparticles are believed to improve the uptake and processing of adsorbed antigen by antigen presenting cells (APCs). Briones, M., et al. 2001. "The preparation, characterization, and evaluation of cationic microparticles for DNA vaccine delivery." *Pharm. Res*. 18:709-712. Denis-Mize, K. S., et al. 2000. "Plasmid DNA adsorbed onto cationic microparticles mediates target gene expression and antigen presentation by dendritic cells." *Gene Ther*. 7:2105-2112. Denis-Mize, K. S., et al. 2003. "Mechanisms of increased immunogenicity for DNA-based vaccines adsorbed onto cationic microparticles." *Cell Immunol*. 225:12-20. O'Hagan, D., et al. 2001. "Induction of potent immune responses by cationic microparticles with adsorbed human immunodeficiency virus DNA vaccines." *J. Virol*. 75:9037-9043. Singh, M., et al. 2004. "Charged polylactide co-glycolide microparticles as antigen delivery systems." *Expert. Opin. Biol Ther*. 4:483-491. Singh, M., et al. 1997. "Controlled release microparticles as a single dose hepatitis B vaccine: evaluation of immunogenicity in mice." *Vaccine* 15:475-481. Singh, M., et al. 2001. "Cationic microparticles are an effective delivery system for immune stimulatory CpG DNA." *Pharm. Res*. 18:1476-1479.

Microparticles are prepared using any of several methods well known in the art. For example, in some embodiments, double emulsion/solvent evaporation techniques, such as those described in U.S. Pat. No. 3,523,907 and Ogawa et al., *Chem. Pharm. Bull*. (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The A Wurster Process@ in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst*. (1988) S(2):99-139; and ionic gelation as described by, e.g., Lim et al., *Science* (1980) 210:908-910.

In preferred embodiments, a water-in-oil-in-water (w/o/w) solvent evaporation system can be used to form the microparticles, along the lines described by O'Hagan et al., *Vaccine* (1993) 11:965-969, PCT/US99/17308 (WO 00/06123) to O'Hagan et al. and Jeffery et al., Pharm. Res. (1993) 10:362.

In general, a polymer of interest, such as PLG, is dissolved in an organic solvent, such as ethyl acetate, dimethylchloride (also called methylene chloride and dichloromethane), acetonitrile, acetone, chloroform, and the like. The polymer will typically be provided in about a 1-30 wt %, more typically about a 2-15 wt %, even more typically about a 3-10 wt % and most typically, about a 4-8 wt % solution, in organic solvent. The polymer solution is then combined with a first volume of aqueous solution and emulsified to form an o/w emulsion. The aqueous solution can be, for example, deionized water, normal saline, a buffered solution, for example, phosphate-buffered saline (PBS) or a sodium citrate/ethylenediamine-tetraacetic acid (sodium citrate/ETDA) buffer solution, among others. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention may be adjusted after microparticle formation and prior to administration. Preferably, the volume ratio of polymer solution to aqueous solution ranges from about 5:1 to about 20:1, more preferably about 10:1. Emulsification is conducted using any equipment appropriate for this task, and is typically a high-shear device such as, e.g., a homogenizer.

In some embodiments, one or more additional components are entrapped within the microparticles. For example, an antigen and/or an immunological adjuvant can be entrapped by adding the same (a) to the polymer solution, if in oil-soluble or oil-dispersible form or (b) to the aqueous solution, if in water-soluble or water-dispersible form.

A volume of the o/w emulsion is then combined with a larger second volume of an aqueous solution, which typically contains a surfactant. The volume ratio of aqueous solution to o/w emulsion typically ranges from about 2:1 to 10:1, more typically about 4:1. Examples of surfactants appropriate for the practice of the invention are listed above. Those of ordinary skill in the art may readily select surfactants appropriate for the type of species to be adsorbed. For example, microparticles manufactured in the presence of charged surfactants, such as anionic or cationic surfactants, may yield microparticles with a surface having a net negative or a net positive charge, which can adsorb a wide variety of molecules. For example, microparticles manufactured with anionic surfactants, such as sodium dodecyl sulfate (SDS), e.g., SDS-PLG microparticles, may adsorb positively charged species, for example, polypeptide-containing species such as proteins. Similarly, microparticles manufactured with cationic surfactants, such as CTAB, e.g., PLG/CTAB microparticles, may adsorb negatively charged species, for example, polynucleotide-containing species such as DNA, RNA or oligonucleotides. Where the species to be adsorbed have regions of positive and negative charge, either cationic or anionic or nonionic surfactants may be appropriate. Certain species may adsorb more readily to microparticles having a combination of surfactants. Moreover, in some instances, it may be desirable to add surfactant to the above organic solution.

Where a cationic surfactant such as CTAB is used, it is typically provided in about a 0.00025-1% solution, more typically about a 0.0025-0.1% solution. Where an anionic surfactant such as DSS is used, it is typically provided in about a 0.00001-0.025% solution, more typically about a 0.0001-0.0025% solution. Where a nonionic surfactant such as PVA is used, it is typically provided in about a 2-15% solution, more typically about a 4-10% solution. For a cationic surfactant, a weight-to-weight surfactant-to-polymer ratio in the range of from about 0.00001:1 to about 0.5:1 is typically used; more typically from about 0.001:1 to about 0.1:1, and even more typically from about 0.0025:1 to about 0.05:1; for an anionic surfactant such as DSS, a weight-to-weight surfactant-to-polymer ratio in the range of from about 0.00001:1 to about 0.025:1 is typically used, more typically from about 0.0001:1 to about 0.0025:1; for a nonionic surfactant such as PVA a weight-to-weight surfactant-to-polymer ratio in the range of from about 0.001:1 to about 0.1:1 is typically used, more typically from about 0.0025:1 to about 0.05:1 is used.

This mixture is then homogenized to produce a stable w/o/w double emulsion. Each of the above homogenization steps is typically conducted at a room temperature (i.e., 25° C.) or less, more typically, for example, while cooling within an ice bath.

Organic solvents are then evaporated. Following preparation, microparticles can be used as is or, for example, lyophilized for future use.

The formulation parameters can be manipulated to allow the preparation of small microparticles on the order of 0.05 $\mu$m (50 nm) to larger microparticles 50 $\mu$m or even larger. See, e.g., Jeffery et al., *Pharm. Res.* (1993) 10:362-368; McGee et al., *J. Microencap.* (1996). For example, reduced agitation typically results in larger microparticles, as do an increase in internal phase volume and an increase in polymer concentration. Small particles are typically produced by increased agitation as well as low aqueous phase volumes, high concentrations of emulsion stabilizers and a decrease in polymer concentration.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Upon preparation, a variety of components can be admixed with the microparticles, including an antigen and/or an immunological adjuvant and the resulting formulation can be lyophilized prior to use if desired. Typically, theses components are added to the microparticles in the context of an aqueous solution or dispersion. In some instances, these species will become adsorbed to the surface of the microparticles (see, e.g., the Examples below in which oligonucleotides, are adsorbed to the microparticle surface). The content of the adsorbed species can be determined using standard techniques.

Thus, the polymer microparticles of the present invention may have a variety of components adsorbed thereon, as well as having a variety of components entrapped or encapsulated within them.

2. Antigens

The immunogenic compositions and kits of the present invention also include one or more *B. anthracis* antigens, which can be, for example, adsorbed on the surface of the polymer microparticles, entrapped within the polymer microparticles, dissolved or dispersed in solution, and/or provided on or entrapped within a separate population of microparticles (including organic microparticles, such as polymer microparticles, or inorganic microparticles, such as aluminum hydroxide microparticles). As indicated above, antigens for use in conjunction with the represent invention include killed, attenuated or inactivated organisms as well as subunit antigens. They include polypeptide containing species, such as proteins and other polypeptides (e.g., protective antigen (PA)), polysaccharide containing species, and polynucleotide containing species which express an immunogenic proteins or polypeptides. Examples of polynucleotide-containing antigens include, for example, (a) nucleic acid sequences that directly encode polypeptide-containing antigens (e.g., mRNA molecules) and (b) vector constructs that indirectly encode polypeptide-containing antigens, for example, vector constructs that express heterologous nucleic acid sequences, which in turn encode polypeptide-containing antigens (e.g., DNA vector constructs and RNA vector constructs).

As indicated above, anthrax vaccine adsorbed (AVA) is the only anthrax vaccine licensed for human use in the U.S., and it is thus a beneficial antigen source for the practice of the present invention. As described in U.S. Patent Application 2004/0082530, the current vaccine is produced from sterile filtrates obtained from batch cultures of *B. anthracis* V770-NP1-R, a production strain derived from the Sterne strain (Sterne (1939). Onderstepoort, *J. Vet. Sci. Anim. Indust.* 13:313-317). The PA-containing filtrate is adsorbed onto aluminum hydroxide (see, e.g., Puziss et al. (1963) *Appl. Microbiol.* 11:330-334). Moreover, a number of alternative procaryotic (bacterial) expression systems have been developed for antigen production, including an *Escherichia coli* expression system (Vodkin et al. (1983) Cell 34:693-697), a *Salmonella typhimurium* expression system (Coulson et al. (1994) Vaccine 12:1395-1401), a *Bacillus subtilis* expression systems (see, e.g., U.S. Pat. No. 6,267,966 to Baillie; Ivins et al. (1986) Infection and Immunity 54:537-542; and Baillie et al. (1994) Let. Appl. Microbiol. 19:225-227), and a number of recombinant *Bacillus anthracis* expression systems that are either asporogenic or unable to produce the LF or EF toxins (see, e.g., U.S. Pat. No. 5,840,312 to Mock et al. and U.S. Pat. No. 6,316,006 to Worsham et al.). Moreover, the complete gene sequence for the *B. anthracis* PA antigen is known (Welkos et al. (1988) Gene 69:287-300) and publicly available, enabling the development and production of a wide variety of antigens, including polypeptide containing and polynucleotide containing antigens. For example, U.S. Patent Application 2004/0082530 describes nucleic acids that contain sequences encoding polypeptide antigens obtained or derived from *B. anthracis*, including sequences encoding the PA antigen and sequences encoding other antigens such as fragments of the EF or LF antigens, which can be inserted into appropriate vector constructs using known techniques.

3. Immunological Adjuvants

In addition to polymer microparticles and at least one type of *B. anthracis* antigen, the immunogenic compositions and kits of the present invention further include (a) at least one polynucleotide-containing immunological adjuvant and (b) optionally, at least one supplemental immunological adjuvant. These immunological adjuvants may be, for example, adsorbed onto the surface of the polymer microparticles, entrapped within the polymer microparticles, dissolved or dispersed in solution, and/or provided on or entrapped within a separate population of microparticles (including organic or inorganic microparticles).

The polymer microparticles, *B. anthracis* antigen, polynucleotide-containing immunological adjuvant, and optional supplemental immunological adjuvant may be administered concurrently with the polymer microparticles and *B. anthracis* antigen, e.g., administered in the same composition or simultaneously administered in two or more separate compositions. Alternatively, these species may be administered sequentially in two or more separate compositions.

Polynucleotide-containing immunological adjuvants for use in conjunction with the present invention include both DNA- and RNA-containing immunological adjuvants, specific examples of which include oligodeoxynucleotides and double-stranded RNA, among others.

CpG oligonucleotides are particularly beneficial polynucleotide-containing immunological adjuvants for the practice of the present invention. As noted above, the phrases "oligonucleotide comprising at least one CpG motif" and "CpG oligonucleotide" refer to a polynucleotide comprising at least one CpG dinucleotide. Oligonucleotides comprising at least one CpG motif can comprise multiple CpG motifs. As used herein, the phrase "CpG motif" refers to a dinucleotide portion(s) of an oligonucleotide, which comprises a cytosine nucleotide followed by a guanosine nucleotide. Guanosine and cytosine analogs (e.g., 5-methylcytosine), can also be used in place of guanosine and cytosine.

Synthetic oligodeoxynucleotides (ODN) containing immunostimulatory CpG motifs are known to n boost the immune response to co-administered antigen(s) (Ag), including AVA. Davis, H. L., et al. 2000. "CpG DNA overcomes hyporesponsiveness to hepatitis B vaccine in orangutans." *Vaccine* 18:1920-1924. Jones, T. R., et al. 1999. "Synthetic oligodeoxynucleotides containing CpG motifs enhance immunogenic vaccine in Aotus monkeys." *Vaccine* 17:3065-3071. Klinman, D. M. 2004. "Immunotherapeutic uses of CpG oligodeoxynucleotides." *Nat. Rev. Immunol.* 4:249-258. Klinman D. M., et al. 2004. "CpG Oligonucleotides improve the protective immune response induced by the anthrax vaccination of rhesus macaques." *Vaccine* 22:2881-2886. Verthelyi, D., et al. 2002. "CpG oligodeoxynucleotides as vaccine adjuvants in primates." *J. Immunol.* 168:1659-1663. CpG ODN induce the functional maturation of professional Ag presenting cells (APCs) and trigger the production of immunostimulatory cytokines and chemokines. Ballas, Z. D., et al. 1996. "Induction of NK activity in murine and human cells by CpG motifs in oligodeoxynucleotides and bacterial DNA." *J. Immunol.* 157:1840-1847. Halpern, M. D., et al. 1996. "Bacterial DNA induces murine interferon-gamma production by stimulation of IL-12 and tumor necrosis factor-alpha." *Cell. Immunol.* 167:72-78. Klinman, D. M., et al. 1996. "CpG motifs expressed by bacterial DNA rapidly induce lymphocytes to secrete IL-6, IL-12 and IFNg." *Proc. Natl. Acad. Sci. USA* 93:2879-2883. Kieg, A. M., et al. 1995. "CpG motifs in bacterial DNA trigger direct B-cell activation." *Nature* 374:546-548.

Unmethylated CpG dinucleotides are relatively common in bacterial DNA, but are underrepresented and methylated in vertebrate DNA. Bird, *Trends Genet.*, 1987, 3, 342-347. Bacterial DNA or synthetic oligonucleotides containing unmethylated CpG motifs are also known to induce immune responses including, for example, B cell proliferation, interleukin-6 and immunoglobulin secretion, and apoptosis resistance. Krieg et al., *Nature*, 1995, 374, 546-549; Klinman et al., *Proc. Natl. Acad. Sci. USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; PCT Publication WO 96/02555; PCT Publication WO 98/16247; PCT Publication WO 98/18810; PCT Publication WO 98/40100; PCT Publication WO 98/55495; PCT Publication WO 98/37919; and PCT Publication WO 98/52581.

CpG oligonucleotides can be prepared using conventional oligonucleotide synthesis techniques well known to the skilled artisan. CpG oligonucleotides can comprise a modified backbone, such as a phosphorothioate or peptide nucleic acid, so as to confer nuclease resistance to the oligonucleotide. Modified backbones are well known to those skilled in the art. See U.S. Pat. Nos. 5,821,060, 5,789,573, 5,736,392, and 5,721,102, Japanese Patent No. 10231290, European Patent No. 839,828, and PCT Publication Numbers WO 98/42735, WO 98/42876, WO 98/36098, WO 98/27105, WO 98/20162, WO 98/16550, WO 98/15648, WO 98/04571, WO 97/41150, WO 97/39024, and WO 97/38013.

CpG oligonucleotides vary widely in size ranging, for example, between 2, 5, 10, 20, 50, 100, 200 and 500 nucleotides. CpG oligonucleotides typically comprise between about 6 and about 100 nucleotides, more typically between about 8 and about 50 nucleotides, even more typically between about 10 and about 40 nucleotides. In addition, CpG oligonucleotides for use in the invention can comprise substitutions of the sugar moieties and nitrogenous base moieties.

As used herein, "dsRNA" refers to double-stranded RNA, which can be obtained from various sources. A number of organisms naturally produce dsRNA, including yeasts and viruses. dsRNA from such sources is generally made up of intermittent riboguanylic acid-ribocytidylic acid ([rG-rC]) and riboadenylic acid-polribouridylic acid ([rA-rU]) base pairs. It is believed that all viruses except single-stranded DNA viruses, produce dsRNA. Viral dsRNA generally exists either in the form of duplexes of complementary RNA strands or in the form of intramolecular secondary structure within single-stranded RNA. Viral sources of dsRNA for dsRNA viruses (genomic), ssRNA viruses (transcription intermediates), dsDNA viruses (symmetrical transcription followed by RNA-RNA annealing), and retroviruses (secondary structure in viral mRNA) are known and described in, e.g., Majde, J.A., *J. Interfer. Cytokine Res.* (2000) 20:259-272 and Jacobs and Langland, *Virology* (1996) 219:339-349. Particular sources of viral dsRNA include, but are not limited to, dsRNAs from Mengo virus-infected cells (Falcoff et al., *Antimicrob. Agents Chemother*. (1973) 3:590-598); dsRNAs from reoviruses and fungal viruses (Field et al., *Proc. Natl. Acad. Sci. USA* (1967) 58:1004-1010, De Benedetti et al., *J. Virol*. (1985) 54:408-413); retrovirus dsRNA (Jacobs and Langland, *Virology* (1996) 219:339-349), such as from HIV-1 (Maitra et al., *Virology* (1994) 204:823-827); dsRNA extracted from picornavirus-infected cells (Falcoff et al., *Antimicrob. Agents Chemother*. (1973) 3:590-598); dsRNA from influenza-infected lungs (Najde et al., *Microb. Pathogen*. (1991) 10: 105-115); dsRNA from infected plant cells (Lin and Langenberg, *Virology* (1985) 142:291-298); dsRNA from togaviruses (Stollar, B. D., *Crit. Rev. Biochem*. (1975) 3:45-69); dsRNA from rubella-virus infected cells (Lee et al., *Virology* (1994) 200:307-312); dsRNA from Semliki Forest virus-infected cells (Lee et al., *Virology* (1994) 200:307-312); dsRNA from dengue virus-infected cells (MacKenzie et al., *Virology* (1996) 220:232-240); the dsRNAs known as Larifan (Riga, Latvia) and Ridostin ("Diapharam" NOP "VECTOR," Berdsk, Russia). Any of these various dsRNAs, as well as dsRNAs from other sources, will find use with the present compositions and methods.

DsRNA from infected cells is readily obtained using standard methods of nucleic acid extraction, such as phenol extraction techniques, and as described in several of the publications above. See, e.g., Falcoff et al., *Antimicrob. Agents Chemother*. (1973) 3:590-598; Fayet et al., *Prog. Immuno-biol. Standard*. (1972) 5:267-273; Majde et al., *Microb. Pathogen*. (1991) 10:105-115).

A number of synthetic dsRNAs are also known. They are synthesized using techniques well known and described in the art. Such synthetic dsRNAs include, but are not limited to, polyriboinosinic-polyribocytidylic acid (poly[rI-rC]) and polyriboguanylic-polyribocytidylic acid (poly[rG-rC]) (see, e.g., Michelson et al., *Prog. Nuc. Acid Res. Mol. Biol*. (1967) 6:83-141); polyriboadenylic-polyribouridylic acid (poly[rA-rU]); low molecular weight dsRNA of mixed base composition, such as, but not limited to, a synthetic dsRNA with 309 bp (Haines et al., *J. Biol. Chem*. (1992) 267:18315-18319); as well as the synthetic mismatched dsRNAs described in, e.g., U.S. Pat. Nos. 5,906,980 and 5,258,369. Moreover, dsRNAs with modified backbones can be made using techniques well known in the art. Further information can be found, for example, in commonly owned PCT/JUS02/30423.

Optional supplemental immunological adjuvants for use in conjunction with the present invention include, but are not limited to, the following: (1) aluminum salts (alum), such as aluminum hydroxide, aluminum phosphate, aluminum sulfate, etc.; (2) oil-in water emulsion formulations (with or without other specific immunostimulating agents such as muramyl peptides (see below) or bacterial cell wall components), such as for example (a) MF59 (International Publication No. WO90/14837; Chapter 10 in *Vaccine design: the subunit an adjuvant approach*, Eds. Powell & Newman, Plenum Press 1995), containing 5% Squalene, 0.5% Tween™ 80, and 0.5% Span® 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween™ 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween™ 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., Stimulon™ (Cambridge Bioscience, Worcester, Mass.)) may be used or particles generated therefrom such as ISCOMs (immunostimulating complexes), which ICOMS may be devoid of additional detergent e.g., WO00/07621; (4) Complete Freunds Adjuvant (CFA) and Incomplete Freunds Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) phospholipid adjuvants, including lipopolysaccharide and liposaccharide phosphate adjuvants, for example, monophosphoryl lipid A (MPL), 3-O-deacylated MPL (3dMPL) e.g. GB-2220221, EP-A-0689454, optionally in the substantial absence of alum when used with pneumococcal saccharides e.g. WO00/56358; as well as aminoalkyl glucosamine phosphate compounds such as those described in U.S. Pat. No. 6,355,257; (7) combinations of 3dMPL with, for example, QS21 and/or oil-in-water emulsions, e.g., EP-A-0835318, EP-A-0735898, EP-A-0761231; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g., a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IL-12 (optionally+a sterol) e.g. WO98/57659; (14) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (15) aminoalkyl glucosaminide 4-phosphates (AGP's), see, e.g., Johnson, D. A. et al.; Bioorg. Med. Chem. Lett., 1999 Aug. 2; 9(15):2273-8, (16) imidazoquinolines such as imiquimod (R-837) and resiquimod (R-848), see, e.g., Vasilakos, J. P. et al.; Cell. Immunol. 2000 Aug. 25; 204(1):64-74, (17) lipopolysaccharide mimetics (including monophosphoryl lipid A mimetics), such as non-saccharide phospholipids (e.g., simplified lipid A analogs lacking a disaccharide) described in Hawkins, L. D. et al; J. Pharmacol. Exp. Ther., 2002 February; 300(2):655-61 and U.S. Pat. No. 6,290,973; and (18) other substances that act as immunostimulating agents to enhance the effectiveness of the composition. Muramyl peptides include, but are not limited to, N-acetylmuramyl-L-threonyl-D-isoglutamine (thr-MDP), N-acteylnormuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of immunological adjuvants, see *Vaccine Design, The Subunit and the Adjuvant Approach*, Powell, M. F. and Newman, M. J, eds., Plenum Press, 1995).

4. Formulation and Administration

The compositions of the present invention will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present. A biological buffer can be virtually any solution which is pharmacologically acceptable and which provides the formulation with the desired pH, i.e., a pH in the physiological range. Examples include various buffers including phosphate buffers, citrate buffers, borate buffers, succinate buffers, and histidine buffers, as well as saline buffer combinations, including phosphate buffered saline, Tris buffered saline, Hank's buffered saline, and the like.

Depending on the final dosage form, other excipients known in the art can also be introduced, including mucosal adhesives, binders, disintegrants, fillers (diluents), lubricants, glidants (flow enhancers), compression aids, colors, sweeteners, preservatives, suspending/dispersing agents, film formers/coatings, and flavors.

Once formulated, the compositions of the invention can be administered parenterally, e.g., by injection (which may be needleless). The compositions can be injected subcutaneously, intraperitoneally, intravenously, intraarterially, intradermally, or intramuscularly, for example. Other modes of administration include nasal, mucosal, intraocular, rectal, vaginal, oral and pulmonary administration, and transdermal or transcutaneous applications.

Treatment may be conducted according to a single dose schedule or a multiple dose schedule. A multiple dose schedule is one in which a primary course of administration may be given, followed by one or more additional doses given at subsequent time intervals, chosen, for example, to maintain and/or reinforce the therapeutic response. The dosage regimen may also be, at least in part, determined by the need of the subject and be dependent on the judgment of the practitioner.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Reagents. Phosphorothioate CpG ODN 1555 (GCTAGACGTTAGCGT) (SEQ ID NO:1) and control ODN 1612 (GCTAGAGCTTAGCGT) (SEQ ID NO:2) were synthesized at the CBER core facility. See Gursel, I., et al. 2001. "Sterically stabilized cationic liposomes improve the uptake and immunostimulatory activity of CpG oligonucleotides." *J. Immunol.* 167:3324-3328. All oligodeoxynucleotides (ODN) were free of endotoxin and protein contamination. ODN were adsorbed onto PLG at 1% wt/wt as previously described. Singh, M., et al. 2001. "Cationic microparticles are an effective delivery system for immune stimulatory CpG DNA." *Pharm. Res.* 18:1476-1479. Briefly, PLG microparticles with a co-polymer ratio of 50/50 were emulsified with hexadecyl trimethyl ammonium bromide through a solvent evaporation process. The resultant cationic PLG microparticles were incubated with ODN overnight at 4° C. with gentle shaking followed by washing and freeze-drying, and the amount of ODN adsorbed to PLG microparticles quantitated. Anthrax Vaccine Adsorbed (AVA) was obtained from BioPort Corporation (East Lansing, Mich., USA). Recombinant protective antigen (rPA) was provided by USAMRIID (Fort Detrick, Md., USA) and prepared as described. Ivins, B. E., et al. 1998. "Comparative efficacy of experimental anthrax vaccine candidates against inhalation anthrax in rhesus macaques." *Vaccine* 16:1141-1148. Recombinant lethal factor (rLF) was purchased from Research Diagnostics Inc. (Flanders, N.J.). The toxinogenic (pXO1$^+$), nonencapsulated (pXO2$^-$) Sterne vaccine strain spores of *B. anthracis* (STI) were obtained from USAMRIID and stored at 4° C. Ivins, B. E. et al. 1990. "Immunization against anthrax with aromatic compound-dependent (Aro-) mutants of *Bacillus anthracis* and with recombinant strains of *Bacillus subtilis* that produce anthrax protective antigen." *Infect. Immun.* 58:303-308.

Animals. Specific pathogen free male A/J mice were obtained from the NCI (Frederick, Md., USA). They were housed in sterile micro-isolator cages in a barrier environment, and studied at 8-12 wk of age. All animal experiments were conducted using ACUC approved protocols, and challenge studies were performed in a BL-2 facility.

Immunization and challenge studies. A/J mice were immunized intraperitoneally (i.p.) with AVA formulated in alum ±CpG ODN, PLG or CpG ODN adsorbed onto PLG (CpG ODN-PLG). The mice were bled weekly, and their serum was stored at −20° C. until use. Mice were challenged i.p. with $3 \times 10^2 - 9 \times 10^3$ 50% lethal dose(s) (LD$_{50}$) of STI spores suspended in 0.5 ml sterile phosphate-buffered saline (PBS) (1 $LD_{50}=1.1\times10^3$ STI spores). Survival was monitored for 21 days.

IgG anti-PA ELISA. IgG anti-PA Ab titers were monitored as described. Klinman D M, et al. 2004. *Vaccine* 22:2881-2886. Briefly, 96-well microtiter plates (Immulon 1B, Thermo Labsystems, Franklin, Mass.) were coated with 1 μg/ml of rPA in PBS at 4° C. overnight. The plates then were blocked with 5% non-fat dry milk in PBS containing 0.1% Tween™ 20. Plates were washed, and overlaid with serially diluted serum for 2 h at room temp. After thorough washing, bound Abs were detected by adding HRP-labeled goat anti-mouse IgG, IgG1, or IgG2a (Southern Biotechnology, Birmingham, Ala., USA) followed by ABTS substrate (Kirkegaard & Perry, Gaithersburg, Md., USA). Relative Ab titers were determined by comparison to a standard curve generated using pooled sera from hyper-immunized mice, and were expressed as the reciprocal of the end point dilution which yielded an absorbance value at least 3 times background levels. All samples were analyzed in duplicate.

Toxin neutralizing assay. The toxin neutralizing titers of individual serum samples were assessed by their ability to protect RAW264.7 cells (ATCC, Manassas, Va., USA) from lethal toxin (LTx) with minor modifications from previously described methods. Ivins, B. E., et al. 1998. *Vaccine* 16:1141-1148. RAW264.7 cells were plated at $3\times10^4$ cells/well in 100 μl of glutamine free RPMI medium 1640 containing 10% fetal bovine serum and 2 mM glutamax-1 (Invitrogen Corporation, France). The cells were incubated at 37° C. in a 5% $CO_2$ in air incubator overnight. Serially diluted antiserum was 1:1 (vol/vol) mixed with LTx (100 ng/ml rPA plus 100 ng/ml rLF) at room temp for 30 min to allow for neutralization to occur. 100 μl of this mixture was then incubated with the cells for 6 h at 37° C. Cell viability was determined by monitoring the reduction of MTT (Sigma-Aldrich, St. Louis, Mo.). Results were standardized against known high-titered monkey serum kindly provided by the CDC.

Statistics. Differences in the kinetic development of anti-PA immune responses were determined by two-way ANOVA. Differences in the IgG anti-PA response induced by various vaccine-adjuvant combinations were assessed by one-way ANOVA. Differences in survival were evaluated using Chi-square analysis of Kaplan-Meier curves. Correlation coefficients were determined by linear regression analysis. The predictive value of IgG anti-PA and toxin neutralizing titers on survival was evaluated using 2-parameter logistic regression. Agresti, A., and B. A. Coull. 1996. Order-restricted tests for stratified comparisons of binomial proportions. Biometrics 52:1103-1111.

(CpG ODN-PLG) boost the immunogenicity of AVA. Previous studies established that CpG ODN could act as immune adjuvants when co-administered with AVA. Klinman D M, et al. 2004. *Vaccine* 22:2881-2886. To examine whether CpG ODN adsorbed onto PLG microparticles constituted an even more effective adjuvant, (CpG ODN-PLG) were co-administered to A/J mice with an optimally immunogenic dose of AVA (200 μl). A/J mice were selected for study because they are susceptible to challenge by attenuated STI anthrax spores, allowing the protective activity of the resultant immune response to be examined in a BL-2 facility. Id.

Figure 1A:
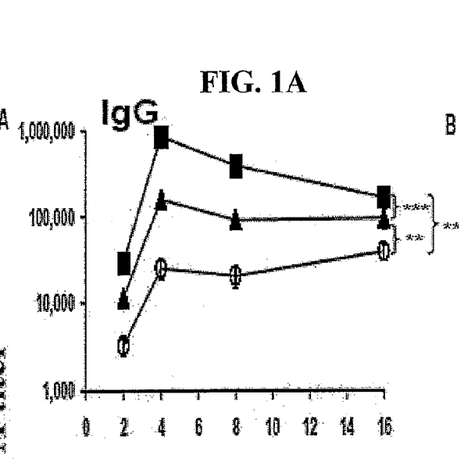
FIGS. 1A-D. IgG anti-PA Ab titers in AVA-vaccinated mice. Male A/J mice were immunized i.p. with 200 µl of AVA (F)+20 µg of free (□) or PLG-adsorbed CpG ODN (O). Data represent the geometric mean SE serum IgG anti-PA titer of 10 independently studied mice/group.  $P<0.01$, * $P<0.001$, ns=not significant, determined by two-way ANOVA. (A) IgG titers vs. weeks post-immunization, (B) IgG1 anti-PA titers vs. weeks post-immunization, (C) IgG2a anti-PA titers vs. weeks post-immunization, (D) TNA titers vs. weeks post-immunization.
Figure 1B:
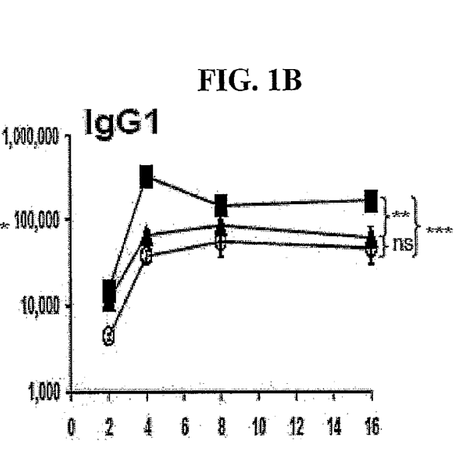
Figure 1C:
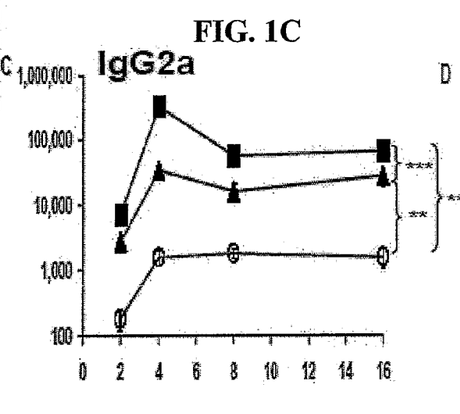
Figure 1D:
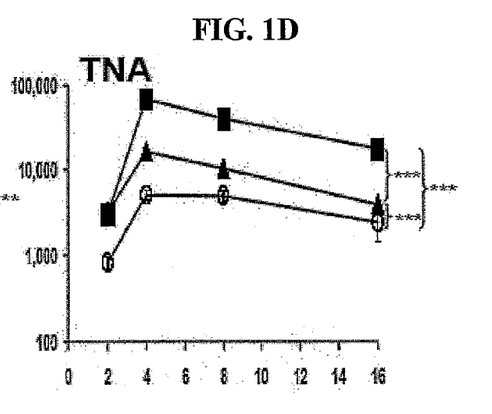

Consistent with previous studies, the magnitude of the IgG anti-PA response induced by AVA was significantly improved by co-administration of CpG ODN (P<0.01, FIG. 1A). However, co-administering (CpG ODN-PLG) with AVA boosted this response by an additional 4-30 fold (P<0.001, FIG. 1A). This improved humoral immune response persisted for the duration of the study (4 months). IgG1, IgG2a, and serum toxin neutralizing Ab (TNA) titers were all significantly increased by combining (CpG ODN-PLG) with AVA (FIG. 1, B-D). IgG anti-PA Ab were undetectable in unvaccinated mice.

Figure 2:
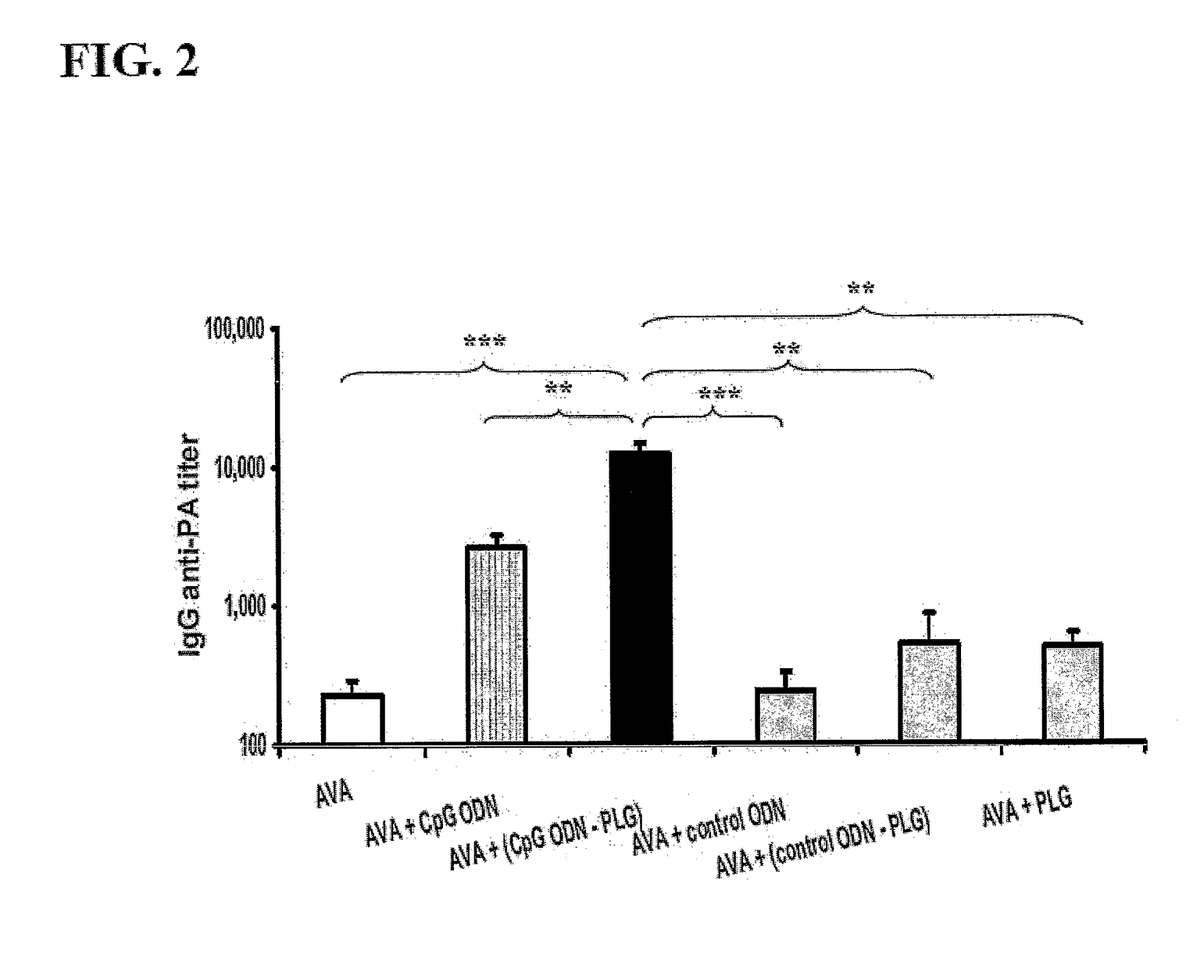
FIG. 2. IgG anti-PA Ab response in A/J mice following low dose AVA (8-25 µl) immunization (i. p.). There were no significant differences in IgG anti-PA titers at these vaccination doses, allowing data from all mice to be combined. Results represent the geometric mean ∀ SE IgG anti-PA response 14 days after immunization (n=11-29 independently studied mice/group).  $P<0.01$, * $P<0.001$, determined by one-way ANOVA.

Antigen-sparing effect of (CpG ODN-PLG). It is possible that the reactogenicity of the licensed anthrax vaccine will be reduced if the amount of AVA required to induce protective immunity is be lowered. Thus, the ability of (CpG ODN-PLG) to reduce the dose of AVA needed to elicit protective immunity was examined. Preliminary experiments established that 8-25 μl of AVA induced a detectable anti-PA response in all vaccinated mice, whereas 3 ul of AVA was immunogenic in only a fraction of vaccinated animals. As seen in FIG. 2, co-administering (CpG ODN-PLG) with 8-25 ul of AVA boosted the resultant IgG anti-PA Ab response by nearly 50-fold when compared to AVA alone (P<0.001, FIG. 2). This effect required the combination of CpG ODN with PLG, since PLG microparticles (alone or in combination with control ODN) had no significant impact on the magnitude of the response induced by AVA (FIG. 2).

(CpG ODN-PLG) accelerate the development of AVA-mediated protection. Preliminary studies demonstrated that mice immunized with 3-8 μl of AVA took >2 weeks required to develop a protective immune response against anthrax infection (data not shown). To determine whether (CpG ODN-PLG) could accelerate this induction of protective immunity, A/J mice were immunized with AVA±adjuvant and their ability to resist anthrax challenge one week later was examined.

Figure 3:
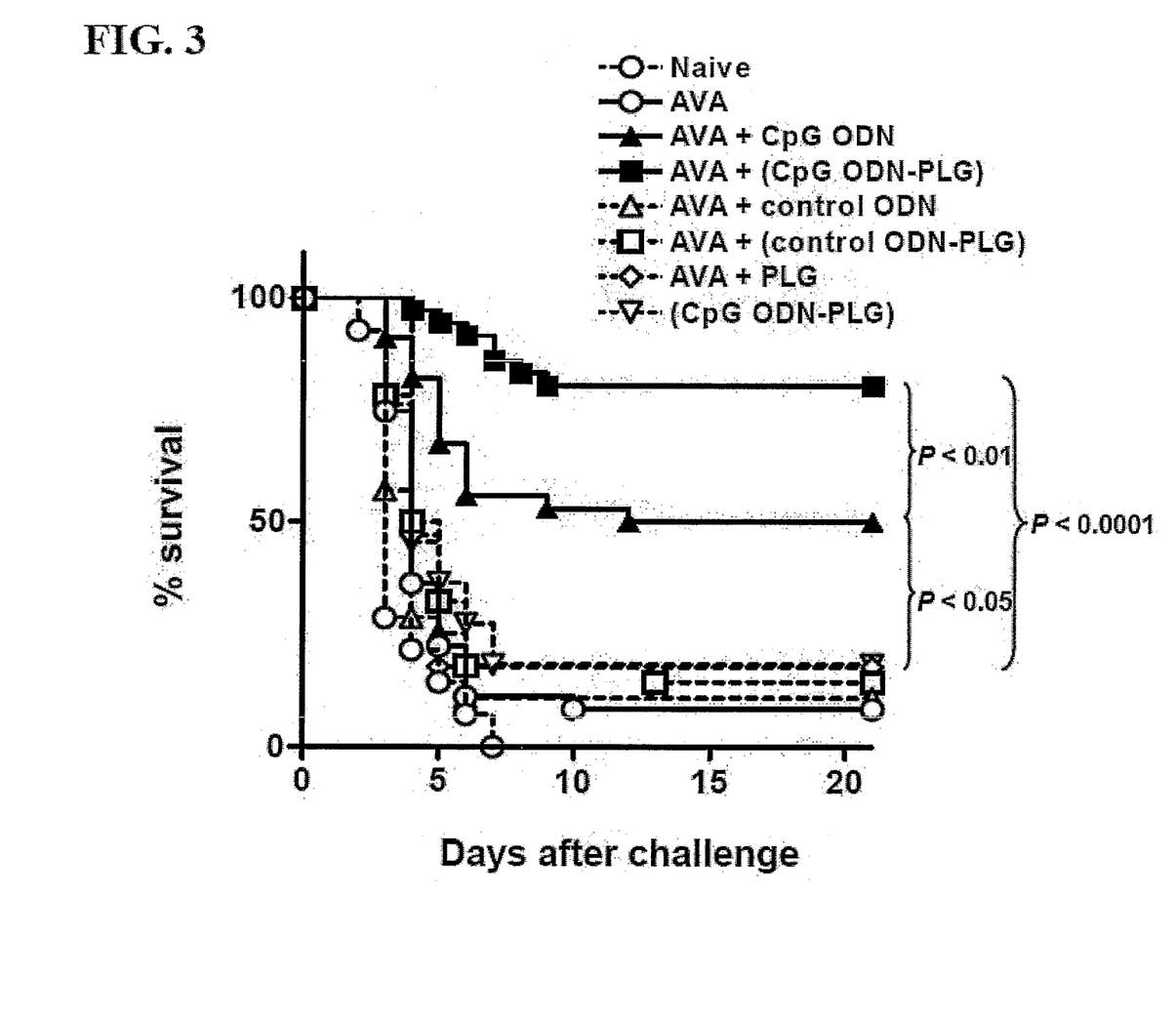
FIG. 3. Survival of vaccinated mice. A/J mice were immunized i.p. with ≤8 µl of AVA plus 20 µg of free or PLG-adsorbed ODN. The mice were challenged i.p. 7 days later with $3\times10^{2-3}$ $LD_{50}$ of STI spores. The survival of control groups (including naive mice and mice vaccinated with AVA) was indistinguishable between experiments. Thus, data from multiple experiments were combined to yield an n=11-36 mice/group.

Consistent with preliminary studies, mice immunized with AVA alone were highly susceptible to infection at this early time point (>90% mortality, FIG. 3). Yet >80% of the mice immunized with (CpG ODN-PLG) plus AVA survived infection at this early time point (P<0.0001, FIG. 3). Immunization with CpG ODN plus AVA in the absence of PLG yielded intermediate protection (50% survival, P<0.01 vs. (CpG ODN-PLG)/AVA, FIG. 3), whereas (CpG ODN-PLG) in the absence of AVA was not protective.

Figure 4A:
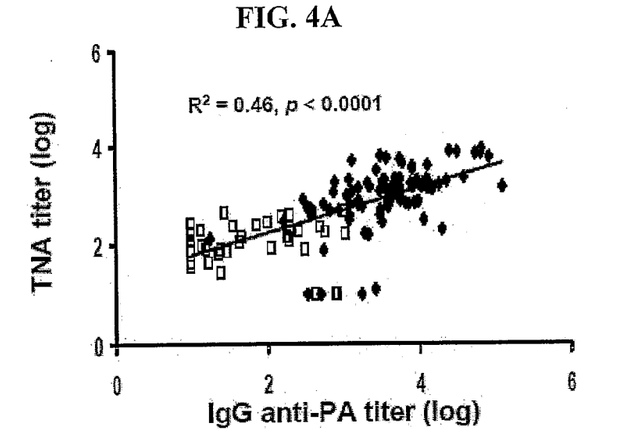
FIGS. 4A-C. Correlation between serum Ab response and survival. Mice were immunized i.p. with 8-25 µl of AVA plus free or PLG-adsorbed CpG ODN. Two weeks post immunization, serum IgG anti-PA and TNA titers were determined, and the mice were challenged i.p. with $9\times103$ LD50 of STI spores. Results from 4 independent experiments involving a total of 130 mice are shown. (A) Linear regression of IgG anti-PA vs. TNA titers in mice that succumbed to (Q) or survived (□) infection. (B) Logistic regression of survival vs. IgG anti-PA titer. (C) Logistic regression of survival vs. TNA titer.
Figure 4B:
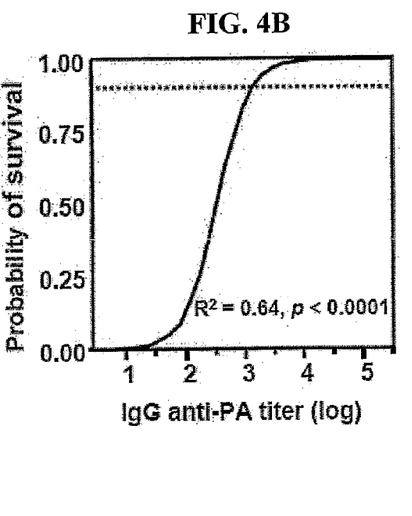
Figure 4C:
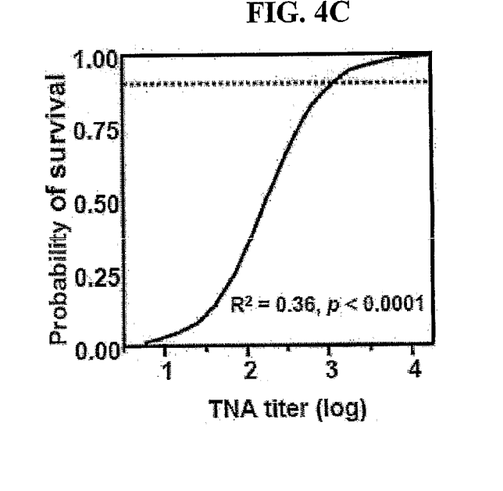

Humoral immunity as a predictor of protection. There is considerable interest in identifying a surrogate marker for protective immunity against anthrax. Towards that end, serum toxin neutralizing activity and IgG anti-PA titer were evaluated as predictors of survival following anthrax spore challenge. As seen in FIG. 4A, TNA correlated significantly with IgG anti-PA titer (2=0.46, P<0.0001). Although TNA predicted protection against anthrax, 2-parameter logistic regression modeling showed that IgG anti-PA was the superior surrogate marker of survival (FIG. 4B, IgG: $R^2=0.64$, P<0.0001; FIG. 4C, TNA: $R^2=0.36$, P<0.0001). In this context, receiver operating characteristic analysis showed that total IgG anti-PA titer was 97% accurate at predicting survival following anthrax challenge, whereas TNA was 91% accurate. The magnitude of the IgG anti-PA response provided valuable information on an animal=s resistance to anthrax infection. For example, >90% of mice are protected against $9\times10^3$ $LD_{50}$ of anthrax if their IgG anti-PA titer exceeds 1,000, while a titer >6,000 indicates that >99% of mice are protected from such high dose challenge.

Conclusions. Current findings indicate that (CpG ODN-PLG) co-administered with AVA results in a more rapid and stronger anti-PA Ab response than immunization with AVA alone or with AVA combined with CpG ODN in the absence of PLG. See FIGS. 1A-D and 2. Significant protection against anthrax challenge was present within one week of vaccination with (CpG ODN-PLG) plus AVA (FIG. 3), indicating that the combination of (CpG ODN-PLG) is significantly more effective as an immune adjuvant than CpG ODN alone or PLG alone. The quality of the resultant anti-PA response was high, as evidenced by enhanced toxin neutralizing activity, improved in vivo protection, and high levels of IgG2a Ab (known to promote the clearance of bacterial infection by complement-mediated cytotoxicity). Oishi, K., et al. 1992. "Antibacterial and protective properties of monoclonal antibodies reactive with *Escherichia coli* O111:B4 lipopolysaccharide: relation to antibody isotype and complement-fixing activity." J. Infect. Dis. 165:34-45. Current results demonstrate that when combined with AVA, (CpG ODN-PLG) boosts and accelerates the resultant immune response, eliciting protective immunity within one week. This response persisted at protective levels throughout the 4 month duration of the experiment (see FIGS. 1A-D and 4A-C).

Although preferred embodiments of the subject invention have been described in some detail, it is understood that obvious variations can be made without departing from the spirit and the scope of the invention.

The invention claimed is:

1. An immunogenic composition comprising: (a) aluminum hydroxide microparticles: (b) an antigen from *Bacillus anthracis* adsorbed onto the aluminum hydroxide microparticles; (c) polymer microparticles comprising a biodegradable polymer; and (d) a polynucleotide-containing immunological adjuvant adsorbed onto the polymer microparticles, wherein the polynucleotide-containing immunological adjuvant is a CpG oligonucleotide and wherein the antigen comprises a subunit antigen which is a polypeptide containing antigen.

2. The immunogenic composition of claim 1, wherein the antigen is from *Bacillus anthracis* strain V770-NP1-R.

3. The immunogenic composition of claim 1, wherein the immunogenic composition further comprises a surfactant.

4. The immunogenic composition of claim 3, wherein the surfactant comprises a cationic surfactant.

5. The immunogenic composition of claim 3, wherein the surfactant comprises an anionic surfactant.

6. The immunogenic composition of claim 1, wherein the polymer microparticles have an average diameter between 500 nanometers and 20 microns.

7. The immunogenic composition of claim 1, wherein the biodegradable polymer is selected from a poly(α-hydroxy acid), a polyhydroxy butyric acid, a polycaprolactone, a polyorthoester, a polyanhydride, and a polycyanoacrylate.

8. The immunogenic composition of claim 7, wherein the biodegradable polymer is a poly(α-hydroxy acid).

9. The immunogenic composition of claim 8, wherein the biodegradable polymer is a poly(D,L-lactide-co-glycolide).

10. The immunogenic composition of claim 9, wherein the biodegradable polymer is a poly(D,L-lactide-co-glycolide) having a lactide:glycolide molar ratio ranging from 40:60 to 60:40.

11. The immunogenic composition of claim 1, wherein the polynucleotide-containing immunological adjuvant comprises an oligonucleotide immunological adjuvant.

12. The immunogenic composition of claim 1, wherein the polynucleotide-containing immunological adjuvant comprises an oligodeoxynucleotide immunological adjuvant.

13. The immunogenic composition of claim 1, wherein the polynucleotide-containing immunological adjuvant is a CpG oligodeoxynucleotide.

14. The immunogenic composition of claim 1, further comprising a supplemental immunological adjuvant.

15. The immunogenic composition of claim 14, wherein the supplemental immunological adjuvant is selected from (a) *E. coli* heat-labile toxins, (b) liposaccharide phosphate compounds, and (c) submicron emulsions comprising squalene and an emulsifying agent.

16. The immunogenic composition of claim 1, wherein the immunogenic composition is an injectable composition.

17. An immunogenic kit comprising: (a) a first composition comprising an antigen derived from *Bacillus anthracis*, wherein the antigen comprises a subunit antigen which is a polypeptide containing antigen, and is adsorbed onto aluminum hydroxide microparticles and (b) a second composition comprising biodegradable polymer microparticles and a polynucleotide-containing immunological adjuvant, wherein the polynucleotide-containing immunological adjuvant is a CpG oligonucleotide and wherein the CpG oligonucleotide is adsorbed onto the polymer microparticles.

18. A method of immunizing a vertebrate host animal against infection by *Bacillus anthracis* comprising administering to the animal the compositions of the kit of claim 17.

19. A method of stimulating an immune response in a vertebrate host animal, comprising administering to the animal the compositions of the kit of claim 17.

20. The method of claim 18, wherein the vertebrate host animal is human.

21. The immunogenic composition of claim 1, wherein said antigen is the protective antigen (PA) of *Bacillus anthracis*.

22. A method of immunizing a vertebrate host animal against infection by *Bacillus anthracis* administering to the animal the immunogenic composition of any one of claims 1, 2, 3-10, 11, 12, 13, 14, 15, 16, and 21.

23. The method of claim 22, wherein the vertebrate host animal is human.

24. A method of stimulating an immune response in a vertebrate host animal, comprising administering to the host animal the immunogenic composition of any one of claims 1, 2, 3-10, 11, 12, 13, 14, 15, 16 and 21.

25. The method of claim 24, wherein the vertebrate host animal is human.

* * * * *